United States Patent [19]

Fahrenkrug et al.

[11] Patent Number: 4,847,134
[45] Date of Patent: Jul. 11, 1989

[54] STRETCHABLE ABSORBENT UNDERGARMENT

[75] Inventors: Anne M. Fahrenkrug, Appleton; Cathy L. Winters, Menasha; Nanette J. Logsdon, Appleton, all of Wis.

[73] Assignee: Kimberly-Clark Corporation, Neenah, Wis.

[21] Appl. No.: 137,294

[22] Filed: Dec. 22, 1987

[51] Int. Cl.⁴ ............................................... B32B 3/10
[52] U.S. Cl. ..................... 428/138; 156/163; 156/164; 428/131; 428/152; 428/198; 428/186; 428/913
[58] Field of Search ............... 428/131, 138, 198, 152, 428/913, 186; 156/163, 164; 604/378

[56] References Cited

U.S. PATENT DOCUMENTS

| | | | |
|---|---|---|---|
| 3,695,985 | 10/1972 | Brock et al. | 161/129 |
| 3,770,562 | 11/1973 | Newman | 161/156 |
| 3,793,133 | 2/1974 | Beaudoin et al. | 161/148 |
| 4,013,816 | 3/1977 | Sabee et al. | 428/288 |
| 4,041,203 | 8/1977 | Brock et al. | 428/157 |
| 4,275,105 | 6/1981 | Boyd et al. | 428/198 |
| 4,287,251 | 9/1981 | King et al. | 428/198 |
| 4,411,660 | 10/1983 | Dawn | 604/396 |
| 4,606,964 | 8/1986 | Wideman | 428/152 |
| 4,650,481 | 3/1987 | O'Connor et al. | 604/380 |
| 4,655,760 | 4/1987 | Morman et al. | 604/385 |
| 4,720,415 | 1/1988 | Wielen et al. | 428/152 |

FOREIGN PATENT DOCUMENTS 86-03964  7/1986  World Int. Prop. O. .

Primary Examiner—James J. Bell
Attorney, Agent, or Firm—John L. Chiatalas

[57] ABSTRACT

The stretchable undergarment comprises a liquid-previous bodyside layer, liquid-impervious outer layer, an absorbent layer, and a stretchable layer. The stretchable layer is stretch-bonded to the other layers and, upon relaxing the stretchable layer forms a plurality of rugosities in the bodyside layer, outer layer, and absorbent medium. The bonded layers are of a generally trapezoidal shape and have a front end portion that diverges toward a rear end portion, wherein the front end portion is from about 20% to about 90% of the width of the rear end portion, and the rear end portion is about 20% to about 60% of the length of the bonded layers.

20 Claims, 11 Drawing Sheets

STRETCHABLE ABSORBENT UNDERGARMENT

BACKGROUND OF THE INVENTION

The present invention relates to absorbent articles or garments, and more particularly to a stretchable absorbent undergarment intended to be worn for absorbing and retaining liquids and waste material.

Currently, there are numerous kinds of wearable garments intended for use as, for example, infant diapers and adult incontinence garments. Some of these garments are reusable, while others are disposable. Regardless of the disposability of the garment, the garment is generally intended to provide several key features such as good absorbency, containment of liquids and waste materials, dry and wet integrity, dry and wet flexibility, surface dryness, low flowback properties, comfort, fit and discreteness.

Probably the single most important feature to the wearer is containment. One approach to achieving superior containment is to focus on improving the absorbent characteristics of the garment. Development of transfer layer structures and the incorporation of superabsorbent materials are two such examples. Even with these advances, containment continues to be the primary issue to the consumer. Looking beyond these absorbency characteristics, another approach is to define the manner with which the undergarment interacts with a body, and to identify the deficiencies of the conventional absorbent products. Several key areas impacting containment are discussed below.

To the degree the undergarment conforms and responds to the body and changing body geometries as movement occurs, its fit is affected. Naturally, containment will improve with a greater or more intimate fit between the undergarment and the body. Several methods, such as folding, elasticizing and molding, have been used in the preshaping of a predominantly planar garment to form a contoured three-dimensional garment for better fit. However, difficulties with each method exist. For example, folding results in a design or configuration which is subject to areas of gapping and fluid channeling along the fold lines. Elasticizing leg areas forms an improved snugging fit, which is generally only effective at the leg openings. Although a molded product appears to offer improved performance, it is currently limited to providing protection for the female body.

Another area influencing containment is pad deformation. The degree to which a garment can maintain its prewear and/or prewet shape directly impacts on its capacity to absorb and contain fluid. For example, it is known that wood pulp-based absorbents tend to become redistributed during body movement, thereby decreasing absorbency in the areas of maximum wetting.

Many current absorbent products or garments are layered materials that are peripherally bonded, but allow shifting between layers. However, rapid absorption or transfer of fluid through multiple layers is enhanced by close contact between those layers. Thus, these absorbent products or garments that are only peripherally bonded create gappnng or separation between layers that reduces the fluid transfer and absorbent rates, thereby degrading the containment characteristic of the product.

One of the recurring problems with current absorbent garments is that they sacrifice one or more of the earlier-mentioned key features in order to possess or increase the effect of others. For example, absorbency generally can be maximized with a combination of fluff and superabsorbent, but one of the problems with this combination is its integrity. When dry, fluff tends to be redistributed by movement or activities of the wearer, thereby decreasing its absorbency in the areas of maximum wetting. Similarly, after wetting, the combination tends to gather or cluster into separate masses of wetted fluff, which is very uncomfortable and visibly embarrassing to the wearer.

One solution to the above problem is to provide a mechanism that maintains the integrity of the absorbent material, such as by introducing amounts of binders, synthetic fibers or the like. Though this may increase dry and wet integrity, it generally causes a decrease in flexibility, which to the wearer translates into a relatively stiff-feeling mat or structure.

SUMMARY OF THE INVENTION

The present invention provides a stretchable absorbent undergarment for absorbing human liquids and waste materials and which has improved fit, integrity, surface dryness and minimal pad deformation. The overall stretchability of the entire undergarment provides an added flexibility as it relates to fit. The undergarment conforms to any body geometry and accommodates both a male and female fit. Since the entire undergarment, rather than a portion or peripheral edge only, responds to movement, it provides a self-adjusting fit during body movements. Also, the undergarment fits a wide range of sizes, and since the material lends itself to an underwear-like fit, it imparts the psychological suggestion of normalcy rather than a diaper-like device.

The undergarment provides increased surface dryness due to the formation of rugosities caused by the stretchable layer. These rugosities provide more available surface area for absorbing fluids, thereby increasing the rate of absorbency. The intimate contact of the undergarment with the body in combination with the overall bulking caused by rugosities also positively affects its absorbency characteristics. The rugosities provide a distancing or separation of the fluid from the body; thus, the body surface is dryer and the wearer perceives increased fluid containment in the absorbent structure. Another positive effect is the minimizing of any wet collapse of the absorbent structure should wood pulp fibers be a component thereof.

In one form of the invention, there is provided a stretchable undergarment for absorbing human liquids and waste materials comprising a liquid-pervious bodyside layer, a liquid-impervious outer layer, an absorbent layer, and a liquid-pervious stretchable layer disposed between the liquid-pervious bodyside layer and liquid-impervious outer layer. The stretchable layer is stretch-bonded to the other layers and forms a plurality of rugosities in the bodyside layer, outer layer and absorbent layer upon relaxation. The bonded layers are of generally trapezoidal shape and have a front end portion that diverges toward a rear end portion, with the front end portion being about 20% to about 90% of the width of the rear end portion, which is about 20% to about 60% of the length of the bonded layers.

BRIEF DESCRIPTION OF THE DRAWINGS

The above-mentioned and other features and objects of this invention, and the manner of attaining them, will become more apparent, and the invention itself will be better understood by reference to the following description of an embodiment of the invention taken in conjunction with the accompanying drawings, wherein.

DEFINITIONS

As used herein and in the claims, the term "elastic," "elastic characteristics," "stretch" and "stretchable" are used interchangeably to define a material or composite which can be elongated by at least 25% of its relaxed length, i.e., elongated to at least 1¼ times its relaxed length (an elongation of 25%), and which will recover upon release of the applied force at least 10% of its elongation. According to this definition, upon release of the applied force at 25% elongation, the material or composite must recover to at least about a 15% elongation. For example, a material or composite is deemed to be "elastic" if a sample length of 100 centimeters can be elongated to a length of at least 125 centimeters, and upon release of the applied force recovers to a length of not more than about 115 centimeters. Many elastic or stretchable materials or composites can be elongated by more than 25% of their relaxed length, and many of these will recover to, or close to, their original relaxed length upon release of the applied force. This latter class of materials is generally preferred for purposes of the present invention. These materials can include not only webs of elastic or stretchable films, such as cast or blown films, but also nonwoven fibrous elastic webs such as meltblown elastomeric fibrous nonwoven webs.

The term "bonding" can mean the joining, adhering, connecting, attaching or the like of two layers or composites, either directly or indirectly together. For example, three layers are directly bonded together if the bond is effective throughout the three layers. These three layers are also said to be bonded if, for example, the outermost two layers are directly bonded along their peripheries so as to capture or sandwich the middle layer therebetween.

The term "transfer layer" refers to a layer of material that primarily directs fluid flow in the Z-direction, which is the direction through the thickness of the layer.

The term "wicking layer" refers to a layer that primarily directs liquid flow in multiple directions in the X-Y plane, which is the plane defined by the length and width of the layer.

DETAILED DESCRIPTION

Figure 1:
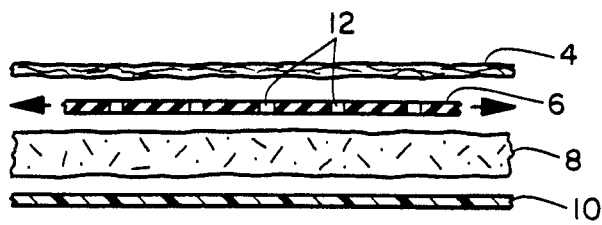
FIG. 1 illustrates one embodiment of the composite before the layers are joined together.
Figure 2:
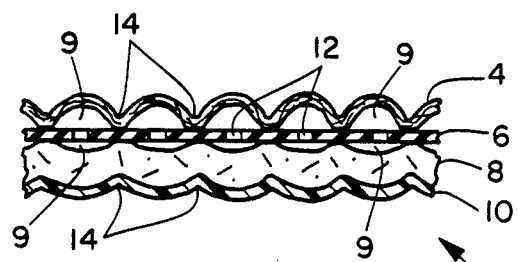
FIG. 2 is the embodiment of FIG. 1 after the layers have been joined together.

Referring to FIGS. 1 and 2, one embodiment of the stretchable absorbent composite 2 comprises liquid-permeable bodyside liner 4, liquid-permeable stretchable or elastomeric layer 6, absorbent medium 8 and liquid-impermeable outer cover 10. In this particular embodiment, elastomeric layer 6 is made permeable by a plurality of apertures 12 disposed therein.

Figure 5:
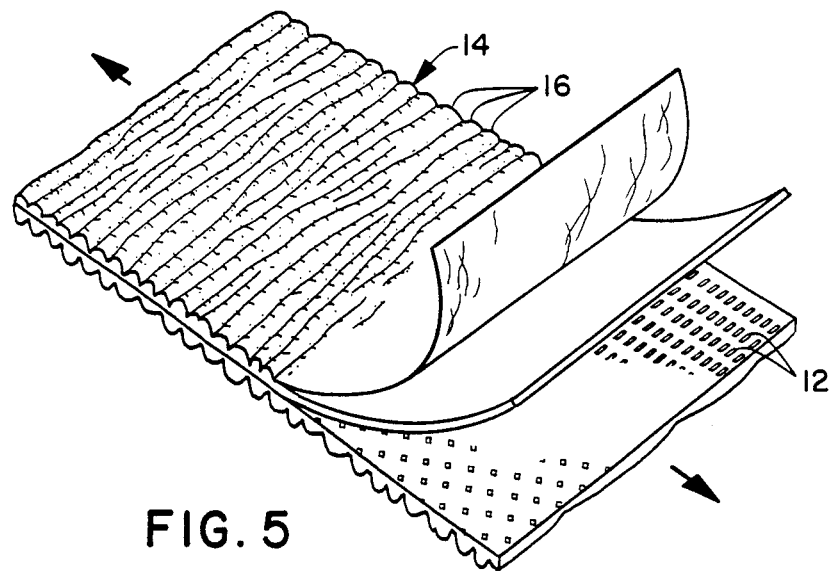
FIG. 5 is a perspective view of the embodiment in FIG. 4 with the top two layers peeled back in order to view the apertures in one of the layers.
Figure 5A:
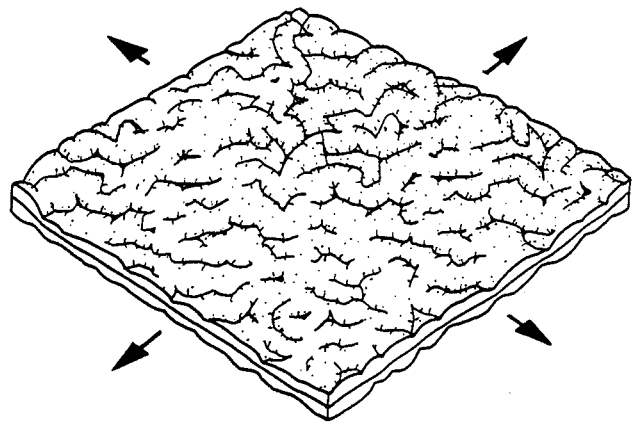
FIG. 5A is a multi-directional stretchable absorbent composite.
Figure 23:
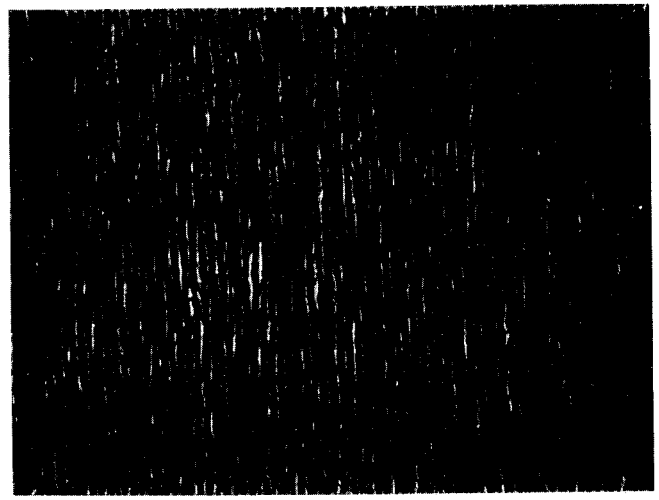
FIG. 23 is similar to FIG. 22 of the other side.
Figure 24:
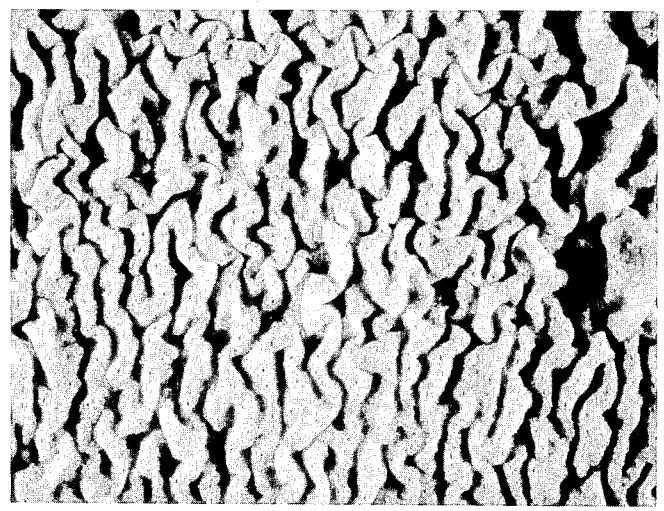
FIG. 24 is a photographic plan view of one side of a multi-stretched composite or undergarment.
Figure 25:
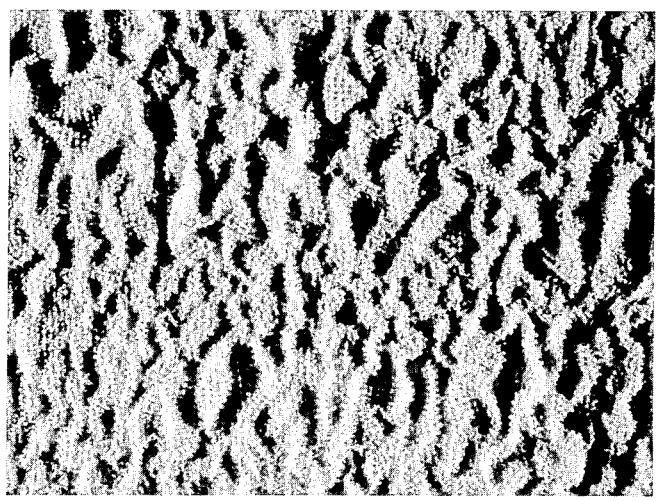
FIG. 25 is similar to FIG. 24 of the other side.

FIG. 1 illustrates composite 2 with the layers separated and the stretchable or elastomeric layer 6 in its relaxed, unstretched condition. In the manufacture of composite 2, which will be described in greater detail below, elastomeric layer 6 is stretched to a desired elongation, and then liner 4, elastomeric layer 6, absorbent assembly 8 and cover 10 are bonded together. After the bonding, composite 2 is relaxed so that elastomeric layer 6 will recover from its stretched state. In doing so, liner 4, absorbent medium 8 and outer cover 10 are gathered, as illustrated in FIG. 2, to form a plurality of rugosities 14 and a plurality of air pockets 9 on either side of elastomeric layer 6 within or inside composite 2. Naturally, rugosities 14 inherently form or create air spaces between one another. When elastomeric layer 6 is elongated in a single direction, such as the machine direction indicated by arrows in FIG. 5, the rows 16 (FIGS. 5 and 22, 23) of rugosities 14, and air pockets 9, are generally perpendicular to the direction, i.e., machine direction of elongation of elastomeric layer 6. If elastomeric layer 6 is multi-directionally elongated, for example, in the X- and Y-directions, then the finished stretchable absorbent composite 2 has a quilted-like or wormy pattern, as illustrated in FIGS. 5A and 24, 25.

Figure 5B:
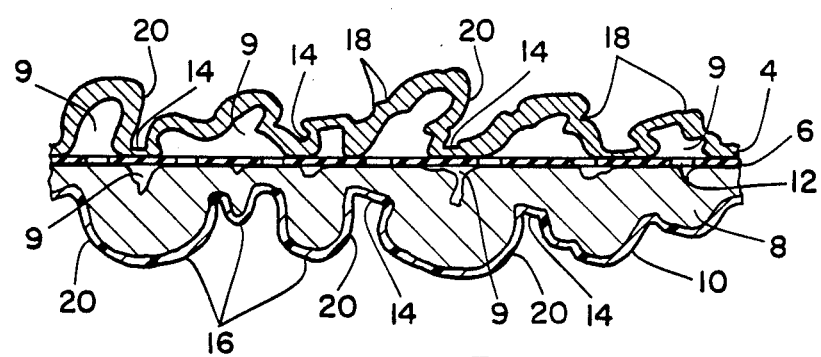
FIG. 5B is an enlarged cross section through FIG. 2.

FIG. 5B illustrates an enlarged cross-sectional view through composite 2 in FIG. 2. Because elastomeric layer 6 is in its relaxed, unstretched condition, liner 4, absorbent 8 and cover 10 have been gathered into a plurality of rows 16 of rugosities 14. Since these layers, i.e., liner 4, absorbent 8 and cover 10, are gathered into rugosities 14, there is a greater amount of surface area per square inch than if the layers were flat or planar. Furthermore, each rugosity 14 has a plurality of smaller or finer wrinkles 18 in its opposite surfaces 20 which extend outwardly relative to elastomeric layer 6. Both rugosities 14 and wrinkles 18 are formed upon relaxing elastomeric layer 6, but they have been differentiated herein to distinguish the larger irregularities of rugosities 14 with the finer irregularities of wrinkles 18. Wrinkles 18 also serve the same purpose as rugosities 14 in providing a larger surface area per square inch of composite 2, as compared to a flat or planar surface.

Since stretchable absorbent composite 2 has a greater surface area per square inch, due to rugosities 14, wrinkles 18, and air pockets 9, it has been discovered that the functions of the particular layers are surprisingly increased. For example, because liner 4 is gathered into a bulky condition, it has a greater surface area per square inch which results in increased body surface dryness. Naturally, the greater the surface area of a liquid-receiving layer, the greater amount of liquid the layer can act upon. Similarly, absorbent 8, because of rugosities 14, wrinkles 18, and pockets 9, has an improved capacity per unit area for receiving, absorbing and retaining liquid. Again, because of the increased surface area per square inch of absorbent medium 8, it is better able to handle or manage greater amounts of liquid, as compared to a flat or planar absorbent of the same finished dimensions.

With reference to outer cover 10, the rugosities 14 and wrinkles 18 provide a cover that is quieter during body movement and present a cloth-like appearance.

Liquid permeable bodyside liner 4 can be a nonwoven web or sheet of polyolefin fibers, such as polypropylene, polyester, polyethylene, Rayon, Chisso and the like. Liner 4 can also be a nonwoven web of synthetic or natural fibers or a blend thereof, a plastic film with perforations or an expanded plastic webbing material or a scrim material. Preferably, liner 4 is spunbonded polyethylene or spunbonded polypropylene having a basis weight of about 0.2 to about 1.0 ounces per square yard. More preferably, liner 4 is spunbonded polypropylene having a basis weight of about 0.2 to about 1.0 ounces per square yard. The material of which liner 4 will be made for any specific embodiment or variation can vary depending upon the exact properties or characteristics desired of liner 4. Generally, it is desired that liner 4 be hydrophobic and have high fluid transfer rates, such as a penetration rate of about 0.05 to about 8.0 ml/sec/cm$^2$, and preferably about 0.5 to about 2.5 ml/sec/cm$^2$. Liner 4 also exhibits good hand properties.

A wide variety of materials can be employed as elastomeric layer 6 and include not only webs of elastic films, such as cast or blown films, but also nonwoven fibrous elastic webs such as, for example, meltblown or spunbonded elastomeric fibrous nonwoven webs. Elastomers may be incorporated into any one of the layers, for example, a meltblown liner, staple coform absorbent, or film. Other materials, such as self-adhering elastomeric materials and extrudable elastic films that shrink and become elastic when cooled, are also suitable for use as elastomeric layer 6. A useful material for making elastomeric layer 6, and most preferably for making meltblown elastomeric fibers, is a block copolymer having the general formula A-B-A' wherein A and A' are each a thermoplastic polymer endblock or segment which includes a styrenic moiety and B is an elastomeric polymer midblock such as a conjugated diene or lower alkene. Materials of this general type are disclosed in U.S. Pat. No. 4,333,782, issued June 8, 1980 to H. A. Pieniak. Similar materials are disclosed in U.S. Pat. No. 4,418,123, issued Nov. 29, 1983 to William L. Bunnelle. Commercially available A-B-A' block copolymers having thermoplastic polystyrene endblocks or segments and a saturated or essentially saturated poly(ethylene-butylene) midblock B or segment, sometimes referred to as an S-EB-S polymer, are available under the trade designation KRATON G, for example, Kraton G-1650, Kraton G-1652, Kraton GX-1657 and Kraton G-2740X, from The Shell Chemical Company. Other examples of elastomeric materials for use in the present invention include polyester elastomeric materials such as, for example, those available under the trade designation Hytrel from E. I. DuPont de Nemours and Company; polyurethane elastomeric material such as, for example, those available under the deiignation Estane from B. F. Goodrich and Company; and polyamide elastomeric material such as, for example, those available under the trade designation Pebax from the Rilsan Company.

Suitable elastic films, as distinguished from an elastic nonwoven web of elastomeric fibers, may also be utilized in accordance with the invention, for example, elastic film sold under the trade name Polytrope by A. Schulman Corporation of Akron, Ohio.

Elastomeric layer 6 is elongatable or stretchable from about 10% to about 800% of its relaxed length, and has good recovery such as at least about 10%. Elastomeric layer 6 also includes apertures 12 that allow rapid fluid passage or transfer therethrough in the direction toward absorbent medium 8 and eliminates or minimizes liquid flow in the reverse direction. Generally, apertures 12 are provided in any manner resulting in the desired fluid transfer properties or rates. Elastomeric layer 6 can also be liquid-permeable due to inherent pores in the material. For example, a meltblown process provides pores in the meltblown product and the addition of a surfactant, if necessary, makes the meltblown product hydrophilic. A preferred basis weight for elastomeric layer 6 is about 10 grams per square meter to about 200 grams per square meter, and a more preferred basis weight is about 60 grams per square meter to about 150 grams per square meter.

Absorbent medium 8 can be made of any suitable absorbent material, for example, a cellulosic material such as an air-formed batt of wood pulp fibers or a batt of meltblown fibers such as polypropylene, polyethylene, polyester and the like. Absorbent medium 8 may also be a bonded carded web of synthetic or natural fibers, a composite of meltblown fibers of polypropylene, polyethylene, polyester mixed with a cellulosic material, or a blend of cellulosic material with staple textile fibers such as Rayon and the like. Absorbent medium 8 may also contain superabsorbent materials to increase its absorbent capacity. Examples of suitable superabsorbent materials include grafted starch, starch polyacrylic acid grafted methyl cellulose, modified polyvinyl alcohols, polyacrylic acid salts that are cross-linked to form absorbent polymers and the like. Absorbent medium 8 may also include layers of different absorbent structure, such as a meltblown layer of polypropylene and a layer of fluff with a superabsorbent material. Absorbent medium 8 may also be made of a foam-type material or a coform material.

In one preferred embodiment, absorbent medium 8 comprises a blend of 70% by weight polyester and 30% by weight of a binder, such as Chisso, having a basis weight of about 70 grams per square meter and mixed therewith a superabsorbent with a basis weight of about 16 grams per square meter.

In another preferred embodiment, absorbent medium 8 is a blend of 60% by weight fluff pulp and 40% by weight polyethylene, having a basis weight of about 150 grams per square meter, with a superabsorbent having a basis weight of about 16 grams per square meter mixed therewith.

Outer cover 10 can be made of any suitable liquid-impermeable material and can also be made of a liquid-impermeable, air-permeable material. Outer cover 10 is preferably made of a polyethylene or polypropylene film having a thickness between about 0.3 to about 1.5 mils and preferably about 0.6 mils. Outer cover 10 can also be a meltblown or film material made of polyethylene, polypropylene or polyolefin copolymers such as ethylene vinyl acetate, ethylene methyl acrylate, ethylene ethyl acrylate, polyvinyl chloride, Nylon and the like. Other acceptable materials include a single spunbonded layer of the above types of materials, two layers of spunbonded and meltblown materials or a three-layer material of spunbonded, meltblown and spunbonded material. Suitable foam materials may also be used as outer cover 10 and include such foams as polyester, polyurethane, and EVA blended with polyester or polyurethane.

Outer cover 10 also has good hand properties.

Although FIGS. 1 and 2 illustrate composite 2 having elastomeric layer 6 between liner 4 and absorbent medium 8, the two can be interchanged such that absorbent medium 8 is adjacent liner 4 and elastomeric layer 6 is adjacent cover 10.

Figure 3:
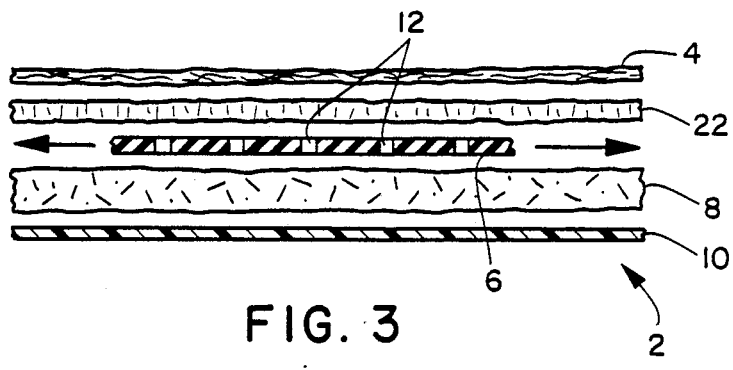
FIG. 3 illustrates another embodiment of the composite before the layers are joined together.
Figure 4:
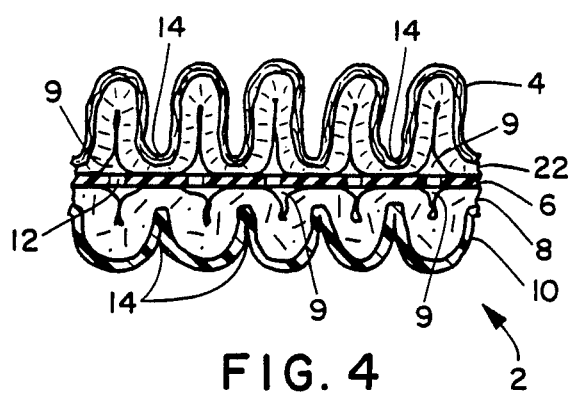
FIG. 4 is the embodiment in FIG. 3 after the layers have been joined together.

Referring now to FIGS. 3 and 4, another embodiment of stretchable absorbent composite 2 is illustrated wherein transfer layer 22 has been added between liner 4 and elastomeric layer 6. One of the purposes of transfer layer 22 is to provide rapid fluid transfer in the Z-direction, which is generally the direction perpendicular to the plane of stretchable absorbent composite 2. By thus providing rapid liquid transfer in the Z-direction, the absorbent rate of stretchable absorbent composite 2 is increased. Transfer layer 22 also preferably has low rewet properties and improved wet resiliency. One method of decreasing rewet properties is by distancing the liner from the absorbent, such as by means of air pockets 9. A method for increasing wet resiliency is the use of synthetic fibers or foams.

Rapid liquid transfer in the Z-direction, which can also be termed the vertical direction with reference to FIGS. 3 and 4, can be accomplished in one manner by orienting the fibers of transfer layer 22 in the Z-direction. This orientation can be accomplished by an air-laying process.

Transfer layer 22 is preferably a nonwoven web made of thermoplastic fibers, such as polyethylene, polypropylene, polyester and the like. Transfer layer 22 can be a bonded carded web, a meltblown web or a spunbond web of thermoplastic fibers or blends thereof. Specifically, transfer layer 22 can be a bonded carded web comprising 70% by weight of polyester fibers and 30% by weight of a suitable binder, such as Chisso, low-melt powders, and the like, and having a basis weight of about 50 grams per square meter. A preferred basis weight range is about 30 to about 70 grams per square meter. Transfer layer 22 can also be a coform material, such as a carded web of polyester bonded to a spunbonded polypropylene carrier sheet and, if desired, a binding agent such as Chisso, low-melt powders, and the like. Specifically, a coform structure comprising 75% by weight polyester as a carded web bonded to a 25% by weight spunbonded polypropylene carrier sheet. The percentage weights of polyester and polypropylene can be varied as necessary or desired.

As with the embodiment of stretchable absorbent composite 2 in FIGS. 1 and 2, the embodiment illustrated in FIGS. 3 and 4 can have transfer layer 22, elastomeric layer 6 and absorbent medium 8 positioned in a different order than illustrated. Any order is acceptable as long as they are between liner 4 and outer cover 10. Preferably, the layers are positioned as illustrated in FIGS. 3 and 4.

Figure 6:
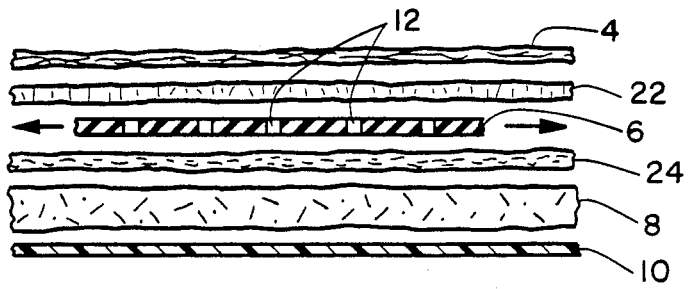
FIGS. 6 and 7 illustrate another embodiment of the composite before and after, respectively, the layers have been joined together.
Figure 7:
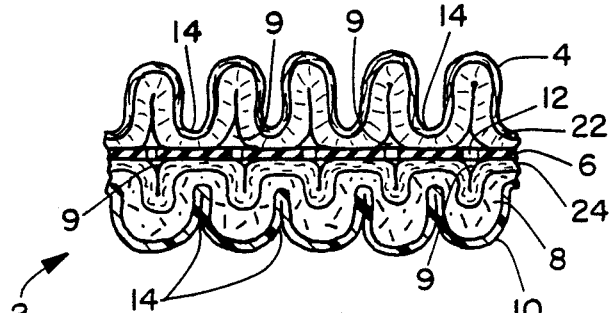

Referring now to FIGS. 6 and 7, another embodiment of stretchable absorbent composite 2 is illustrated wherein wicking layer 24 has been added between elastomeric layer 6 and absorbent medium 8. Wicking layer 24 serves to rapidly transfer liquid in the X- and Y-directions, which are in the plane of composite 2 so as to provide rapid absorption by absorbent medium 8. The rapid transfer of liquid in the X- and Y-direction is provided by orienting the fibers of wicking layer 24 in the horizontal direction, as viewed in FIGS. 6 and 7. In other words, the fibers in wicking layer 24 are generally perpendicular to the fibers in transfer layer 22. This horizontal or X- and Y-orientation of fibers can be attained by various processes, such as wet-laying and carding.

Wicking layer 24 can generally be made of the same type of materials as transfer layer 22.

Wicking layer 24, elastomeric layer 6, and absorbent 8 can be arranged in any order between liner 4 and outer cover 10. However, FIG. 6 illustrates the preferred order of liner 4, transfer layer 22, elastomeric layer 6, wicking layer 24, absorbent medium 8 and outer cover 10.

Figure 8:
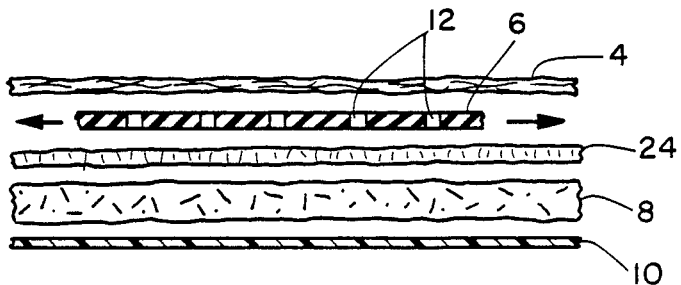
FIGS. 8 and 9 illustrate yet another embodiment of the composite before and after, respectively, the layers have been joined together.
Figure 9:
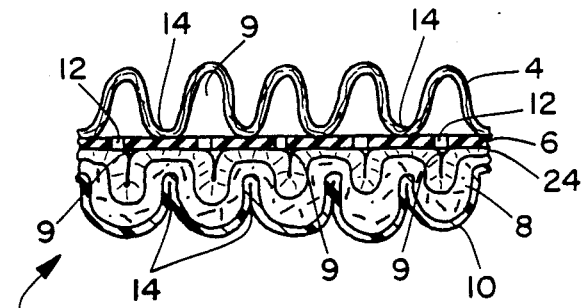
Figure 10:
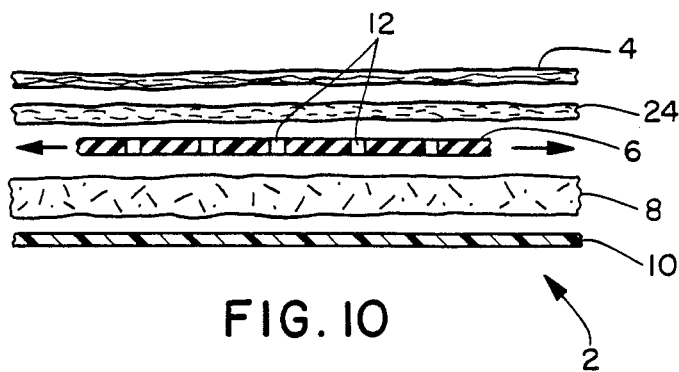
FIGS. 10 and 11 illustrate still another embodiment of the composite before and after, respectively, the layers have been joined together.
Figure 11:
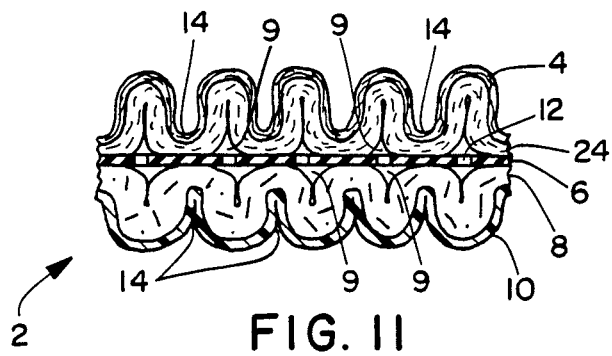

Referring now to FIGS. 8 and 9, still another embodiment of stretchable absorbent composite 2 comprises liner 4, elastomeric layer 6, wicking layer 24, absorbent medium 8 and outer cover 10. Elastomeric layer 6 and wicking layer 24 can be interchanged in position between liner 4 and absorbent medium 8, as illustrated in FIGS. 10 and 11.

Figure 12:
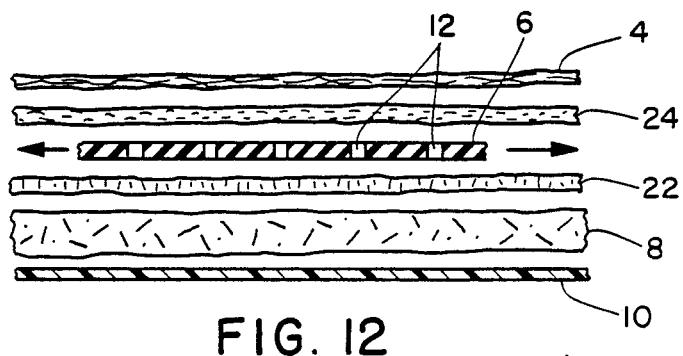
FIGS. 12 and 13 illustrate another embodiment of the composite before and after, respectively, the layers have been joined together.
Figure 13:
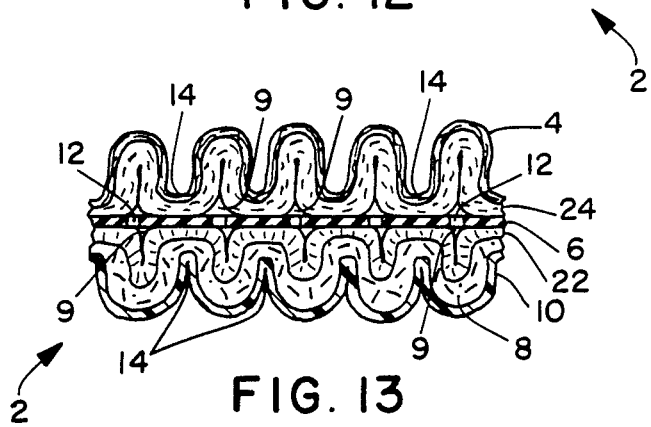

FIGS. 12 and 13 illustrate a variation on FIGS. 6 and 7 wherein layers 22, 24 are interchanged.

Figures 14, 16:
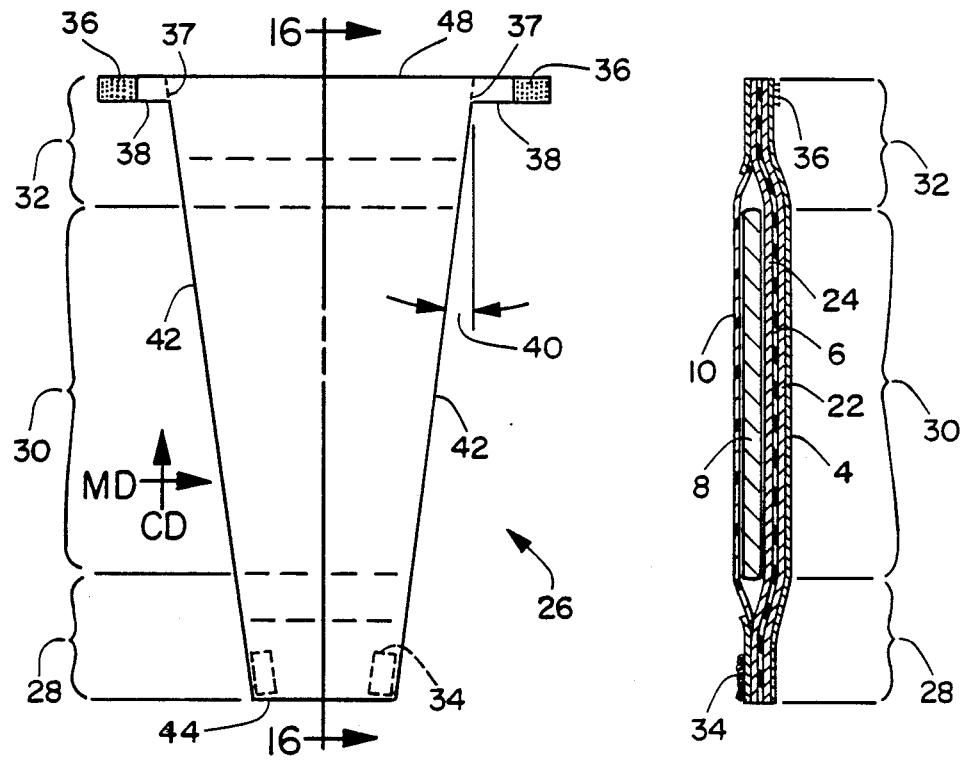
FIG. 14 is a top plan view of an undergarment before the stretchable layer has been relaxed.
FIG. 16 is a sectional view of FIG. 14 taken along line 16—16 and viewed in the direction of the arrows.

Referring now to FIG. 14, stretchable absorbent undergarment 26 is illustrated and is generally trapezoidal in shape. Undergarment 26 in FIG. 14 is in a flat or planar configuration, i.e., elastomeric layer 6 is still in its stretched condition so that the remaining layers are not gathered for purposes of clarity in description. In describing undergarment 26, the length refers to the longer dimension, and includes front end portion 28, intermediate portion 30 and rear end portion 32.

FIG. 16 is a cross-sectional view of FIG. 14 and illustrates outer cover 10, absorbent medium 8, wicking layer 24, elastomeric layer 6, transfer layer 22 and body-side liner 4. In this particular form, only intermediate portion 30 includes all six layers. Although front end portion 28 and rear end portion 32 do not include absorbent medium 8, the present invention contemplates that all of undergarment 26, that is portions 28, 30 and 32, will comprise all six layers. Furthermore, though undergarment 26 in FIGS. 14–16 include the six mentioned layers, it can have a fewer number of layers corresponding to the embodiment of stretchable absorbent composite 2 illustrated in FIGS. 1-4 and 8-11. Thus, undergarment 26 can comprise the four layers in FIG. 2, the five layers in FIG. 4, the six layers in FIG. 6, etc.

Continuing to refer to FIGS. 14 and 16, undergarment 26 has fastening means at front end portion 28 and rear end portion 32, such as a hook and loop fastening means, i.e., Velcro, with loops 34 disposed on front end portion 28 of outer cover 10, and hooks 36 disposed on rear end portion 32 of bodyside liner 4. Naturally, loops 34 and hooks 36 can be interchanged between front end portion 28 and rear end portion 32, and if preferred, only fastening tabs 38, which extend outwardly from rear end portion 32 as viewed in FIG. 14, can have fastening means disposed thereon. Alternative fastening means include suitable adhesives, snap fasteners or the like, all of which should be refastenable, so as to allow undergarment 26 to be removed and replaced any number of times. The fastening tabs 38 can also be eliminated, as at dotted line 37 in FIGS. 14, 15, 17, 18 and 19, so that undergarment 26 is of a true trapezoidal shape. Hooks 36 would then be placed at the corners of rear end portion 32.

Figure 15:
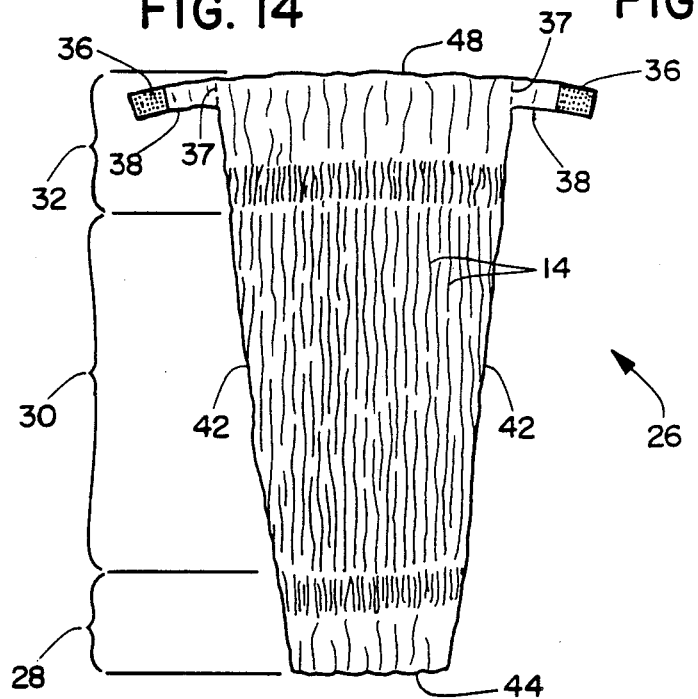
FIG. 15 is similar to FIG. 14 illustrating the effect on the undergarment after the stretchable layer is relaxed.

Referring now to FIG. 15, stretchable absorbent undergarment 26 has been relaxed to allow elastomeric layer 6 to gather the remaining layers into rugosities 14. In the relaxed, gathered state, undergarment 26 has an overall length of about 20 inches to about 50 inches, an overall rear end width as measured between the remote ends of fastening tabs 38 of about 10 inches to about 30 inches, a front end width as measured along the narrowmost edge of front end portion 28 of about 4 inches to about 15 inches and an angular range of about 5° to about 45° as measured between side edges 42 and the vertical, as viewed in FIG. 14.

Figure 17:
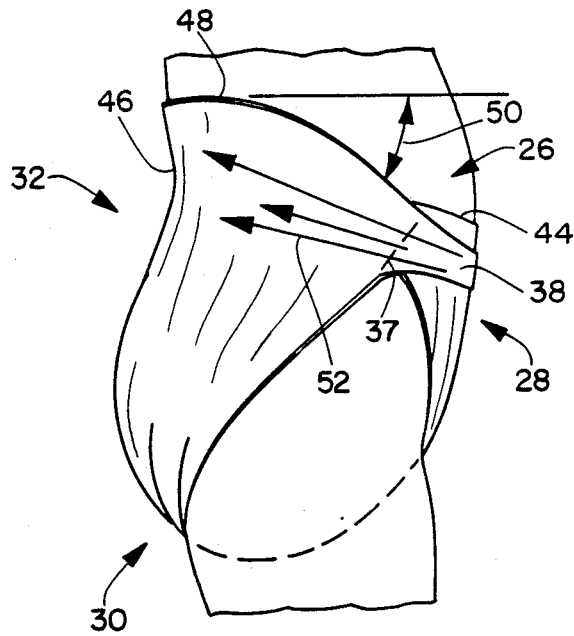
FIG. 17 illustrates the undergarment of FIGS. 14 and 15 as it would appear when worn.
Figure 18:
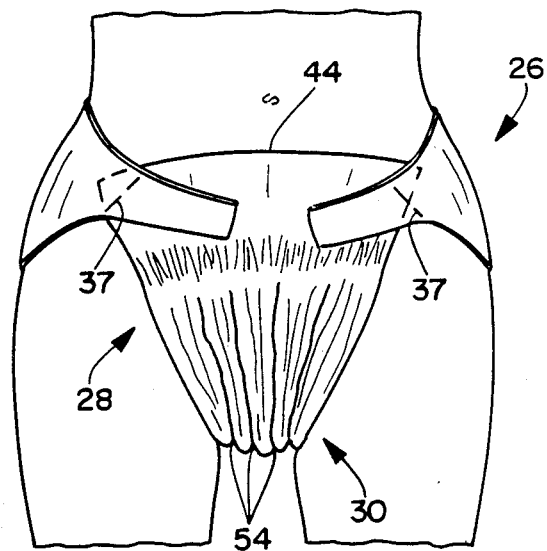
FIG. 18 illustrates a front view of the undergarment when worn.

Referring now to FIGS. 17 and 18, stretchable absorbent undergarment 26 is illustrated as it would be worn by a user. In the side profile view of FIG. 17, front end portion 28 rests against the stomach or abdomen of the wearer with front edge 44 of front end portion 28 being at or just slightly below the waistline, and with central portion 46 of rear end portion 48 being slightly above the waistline and against the small of the back. As thus worn, front edge 44 is generally horizontally disposed. Rear edge 48 extends generally downwardly from central portion 46, which is at the small of the back of the wearer, to front end portion 28 at an angle 50 of about 10° to about 60° with the horizontal, as viewed in FIG. 17. In fitting stretchable absorbent undergarment 26 to the wearer, intermediate portion 30 is placed generally at the crotch area, and front end portion 28 is pulled, i.e., stretched, to fit against the stomach or abdomen, as described above. Rear end portion 32 is then positioned, i.e., stretched, against the small of the back of the wearer, with fastening tabs 38 then releasably fastened to front end portion 28. When properly fitted, virtually all of stretchable absorbent undergarment 26 is under a certain amount or degree of stretch or tension produced by the proper placement, i.e., stretching, of front end portion 28, rear end portion 32 and attachment of fastening tabs 38 to portion 28. Because of this, there are a plurality of force vectors 52 directed generally from front end portion 28 towards central portion 46 that provides an upward pull or tugging fit of intermediate portion 30 at the crotch of the user. Although force vectors 52 are directed angularly upwardly at an angle less than 90°, they nevertheless have Y- or upwardly directed component force vectors, as viewed in FIG. 17. One of the key and unique features of stretchable absorbent undergarment 26 is that it maintains undergarment 26 snugly in place, both before and after a void.

Because of the generally trapezoidal shape of undergarment 26, when it is fitted about the legs, the leg openings tend to form a generally ellipsoidal shape due to the undergarment following the natural contours of the body.

Figure 19:
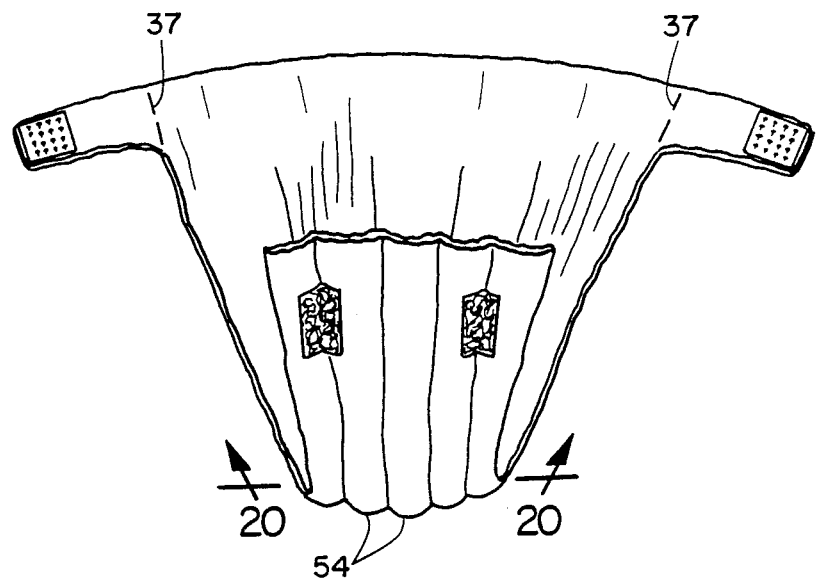
FIG. 19 is a view of the undergarment of FIG. 15 in a partially curved condition it would assume during the placement on a wearer.
Figure 20:
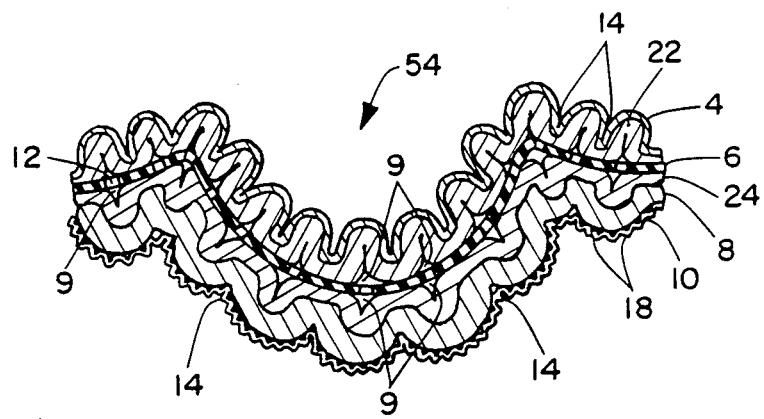
FIG. 20 is a sectional view of FIG. 19 taken along line 20—20 and viewed generally in the direction of the arrows.

Referring now to FIGS. 18, 19 and 20, it can be seen that undergarment 26, when properly fitted, results in a plurality of gross channels 54 at least in intermediate portion 30. Gross channels 54 result from intermediate portion 30 being conformably fitted within the crotch area of the user. Because the crotch area is generally more narrow in width than intermediate portion 30, upon properly fitting undergarment 26, intermediate portion 30 tends to be gathered when fitted in place. Channels 54 act as surge tanks for liquid discharge to hold and maintain the liquid away from the wearer's body until it is completely transferred through liner 4, transfer layer 22, elastomeric layer 6 and wicking layer 24 into absorbent medium 8. Also, because channels 54 run in a generally longitudinal direction relative to the length of undergarment 26, they tend to provide somewhat of a wicking action in moving the liquid along the surface area of intermediate portion 30. This function of channels 54 works in concert with rugosities 14 and wrinkles 18 in spreading or wicking the liquid and transferring it from the user's body into absorbent medium 8.

Gross channels 54 can also be manufactured into undergarment 26 by selective bonding of spaced apart points or lines thereon.

Figure 26:
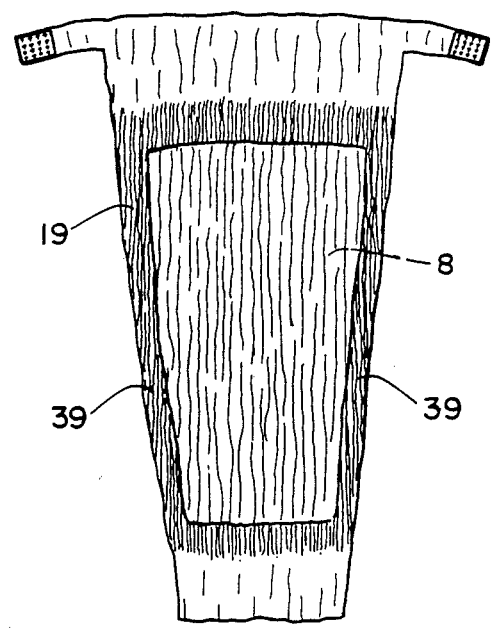
FIG. 26 is similar to FIG. 15 and illustrates a modification to the undergarment.
Figure 27:
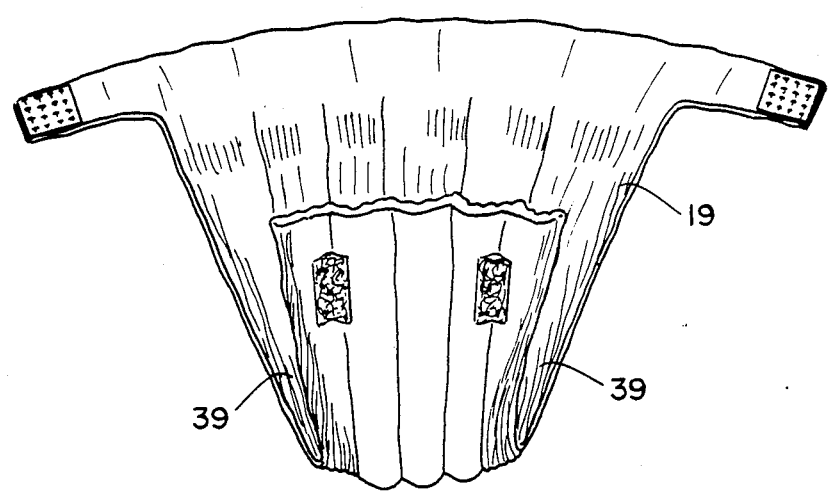
FIG. 27 is similar to FIG. 19 illustrating the modification of FIG. 26.

With reference to FIG. 26, the layers of undergarment 26 can be of various sizes and shapes. For example, in FIG. 26, absorbent medium 8 is similar to, but smaller than, the other layers. This leaves a boundary 39 of the other layers about absorbent medium 8. When elastomeric layer 6 is stretch bonded to all the layers, the stretch bonded boundary 39 about absorbent medium 8 increases the gasketing effect about the legs and decreases possible gapping between undergarment 26 and the body. Another example would be outer cover 10 being smaller than the other layers, but larger than absorbent medium 8 to allow the side portions of cover 10 to overlap absorbent medium 8 to form baffles therearound. This modification results, after the stretch bonding process, in absorbent medium 8 being curved or cupped to form a trough or concave-shape facing the body, thereby providing a conformable fit and improved waste containment. Liner 4, wicking layer 24, transfer layer 22, and elastomeric layer 6 can be variously sized and shaped to provide other changes for any desirable purpose or need. FIG. 27 illustrates the effect of a smaller size absorbent medium 8 at the crotch area. Gross channels 54 are present, as are rugosities 14, but there are now finer rugosities 19 about the leg opening areas to increase gasketing. Rugosities 19 are finer or smaller since absorbent medium 8 is absent at that area.

As described above, it is now apparent that stretchable absorbent undergarment 26 provides an individualized fit over the entire surface area it covers on the user. Undergarment 26 is also a virtually one-size-fits-all undergarment in that if the elastic or stretch characteristics of elastomeric layer 6 are properly selected, undergarment 26 can fit most any size user. For example, if elastomeric layer 6 has at least about 100% stretch or elongation in the machine direction, which is the direction perpendicular to the length dimension of undergarment 26, then rear end portion 32 and tabs 38, if used, can be stretched to accommodate a range of waist sizes from about 20 inches to about 54 inches. As described earlier, rear end portion 32 stretches across the small of the back, rides downwardly over the hips and attaches to front end portion 28, thereby providing an upward snugging force that results in an edge seal at the leg openings 56 to prevent leakage.

The overall elasticity or stretchability of absorbent undergarment 26 provides increased flexibility as it relates to fit. For example, stretchable absorbent undergarment 26 conforms to virtually any body geometry, thereby accommodating both male and female torsos. The entire stretchable absorbent undergarment 26, rather than only a portion or peripheral edge portion thereof, fully responds to movement of the wearer, thereby providing a self-adjusting fit during use. Undergarment 26 further lends itself to an underwear-like fit which imparts the psychological suggestion of normalcy to the user, rather than a diaper-like device.

Because stretchable absorbent composite 2 and stretchable absorbent undergarment 26 contain thermoplastic components in their respective layers, they provide both a dry and wet integrity and resilience, both of which have functional and perceptual benefits. Furthermore, because of the bulking or gathering of resilient materials created by elastomeric layer 6, there is imparted to composite 2 and undergarment 26 the ability or capacity to maintain an original shape, which is a key factor in achieving superior containment. As the post-use shape and bulk resembles the prewear appearance of composite 2 and undergarment 26, there is a reduction in the visual and tactile impact of an incontinent episode. These improved post-use aesthetics also impart a psychological comfort and normalcy to the incontinent user.

Due to the intimate contact of the layers in composite 2 and undergarment 26 in combination with the overall bulking or gathering thereof, the absorbency characteristics of composite 2 and undergarment 26 are positively affected; for example, there is an increase in the rate of fluid transfer from the surface of the wearer to the absorbent medium 8, and a minimizing of any wet collapse or clumping of cellulosic material should wood pulp fibers be a component of absorbent medium 8.

The use of transfer layer 22 and wicking layer 24 provides an increase in absorbent rates at the bond points and controlled flowback properties. A more detailed description of how the absorbent rates are increased at the bond points and the flowback properties minimized can be found in U.S. Pat. No. 4,397,644, filed Feb. 4, 1982, which is incorporated by reference herein.

Other unique features of stretchable absorbent composite 2 and stretchable absorbent undergarment 26 are provided by rugosities 14 and 19, wrinkles 18 and gross channels 54. These three features result or create an increase in absorbency rate because of the greater amount of surface per unit area. Separation of liquid from the body is provided because of rugosities 14 and 19, wrinkles 18 and gross channels 54 which, with air pockets 9, result in increased air circulation between the body surface and the absorbed liquid, thereby providing or maintaining the body surface drier and more comfortable to the wearer. Composite 2 and undergarment 26 are disposable.

Figure 21:
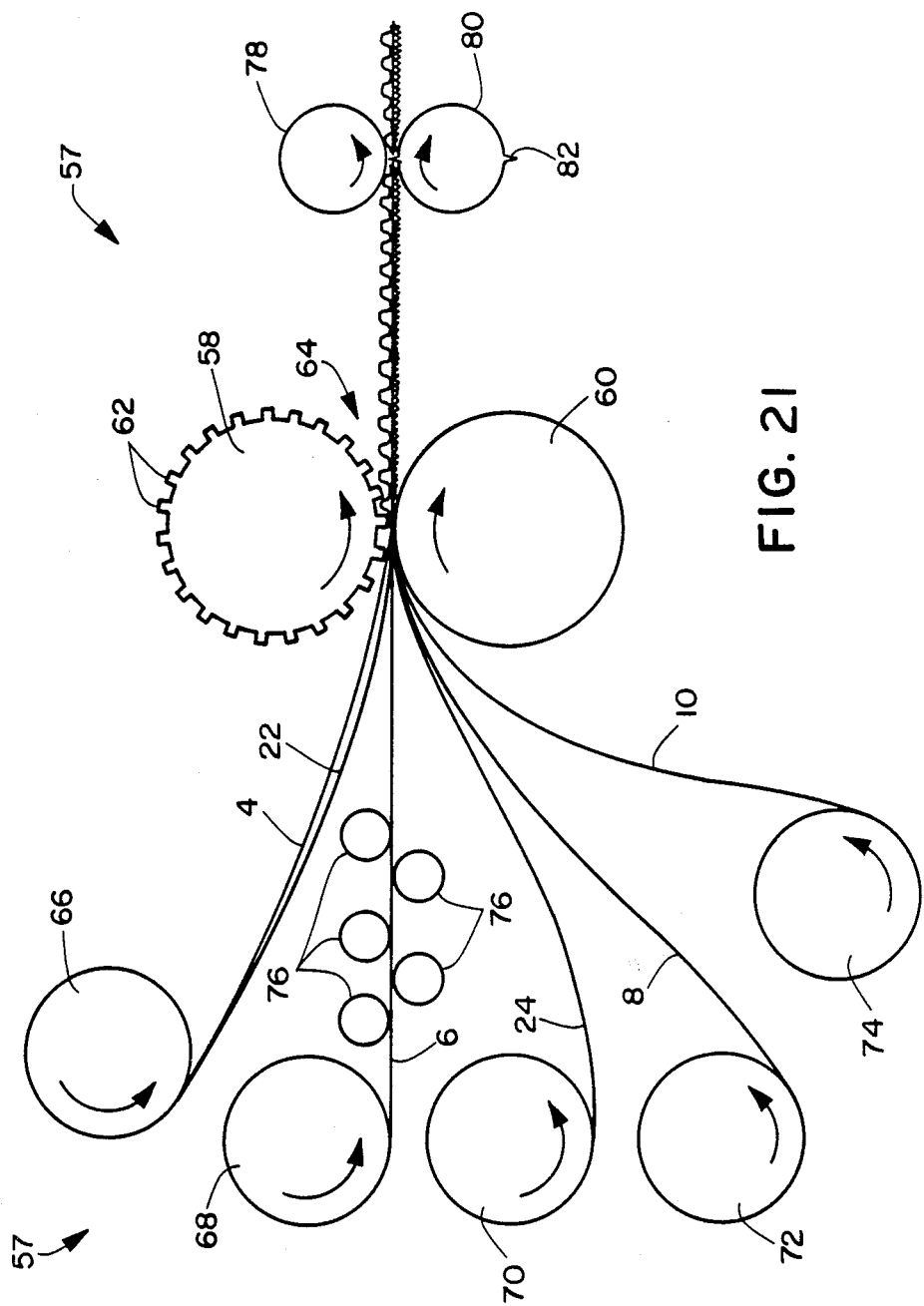
FIG. 21 is a schematic of an apparatus for making an undergarment.

Referring now to FIG. 21, apparatus 57 includes pattern roll 58 having a plurality of projections 62 selectively disposed thereon, and anvil 60 adjacent pattern roll 58 to form nip 64 therebetween. Both pattern roll 58 and anvil 60 are selectively rotatable in the direction of the arrows, and are selectively thermally controlled to provide a selected temperature on their respective outermost surfaces. Furthermore, either pattern roll 58 or anvil 60, or both, are moveable toward the other to vary selectively the pressure applied at nip 64. As mentioned earlier, projections 62 are selectively disposed on pattern roll 58 in any desired pattern, as further described below.

Apparatus 57 also comprises liner-transfer layer roll 66 that provides a two-layer web comprising liner 4 and transfer layer 22, which can be a coform material earlier described above and preformed separately on roll 66. Elastomeric layer roll 68 provides elastomeric layer 6, wicking layer roll 70 provides wicking layer 24, absorbent medium roll 72 provides absorbent medium 8 and outer cover roll 74 provides outer cover 10. The various roll supplies can be interchanged so as to vary the arrangement of the layers, as illustrated in FIGS. 1-13.

Figure 22:
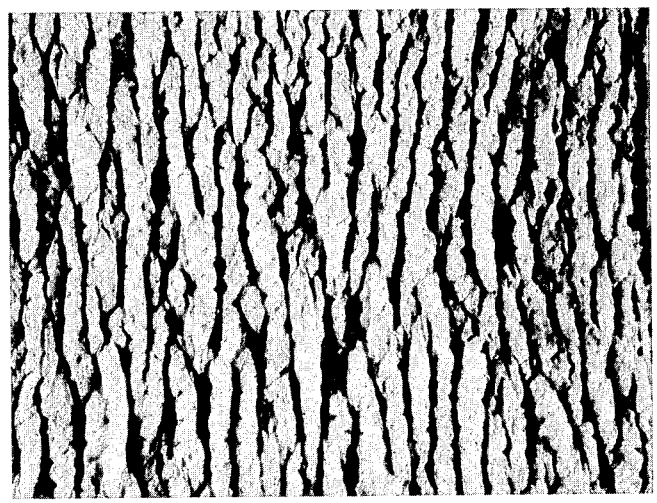
FIG. 22 is a photographic plan view of one side of a unidirectionally stretched composite or undergarment.

In order to stretch elastomeric layer 6 before passing through nip 64, the rate of rotation of elastomeric layer roll 68 is selectively decreased below that of the selected rates of rotation of the other rolls 66, 70, 72 and 74. Because elastomeric roll 68 rotates at a slower speed, elastomeric layer 6 is stretched in the machine direction during its travel from roll 68 through nip 64. If desired, elastomeric layer 6 can also be stretched simultaneously, or only, in the cross-direction by use of stretching rolls 76 or any other known means, such as a tenter frame. Generally, stretching rolls 76 are curved or bowed so as to stretch elastomeric layer 6 in the cross-direction while being pulled thereacross. Control of the direction of stretch or elongation of elastomeric layer 6 is a useful feature not only in tailoring the properties and the shaping of the composite 2 or undergarment 26, but also in the handling and manipulating of composite 2 or undergarment 26 during the manufacturing processes. Naturally, the basis weight and stiffness of elastomeric layer 6 and the other selected layers, and the degree and direction of elongation of layer 6, may be selected to provide the desired properties in the finished composite 2 or undergarment 26. The stretching of elastomeric layer 6 in the machine direction only, or the cross-direction only, results in rows 16 of rugosities 14, as illustrated in FIGS. 5, 22, and 23. Similarly, the stretching or elongation of elastomeric layer 6 in both the machine and cross-direction results in the quilted configuration illustrated in FIGS. 5A, 24, and 25. If desired or necessary, one or all of rolls 76 can be provided with aperturing means, such as sharp or pointed projections, for aperturing elastomeric layer 6, whether it is being uni- or multi-directionally stretched.

As mentioned earlier, projections 62 can be selectively disposed on the outermost surface of pattern roll 58, and in doing so, allows the immobilization of selected areas of the stretchable absorbent composite 2 or stretchable absorbent undergarment 26 so as to control and vary the elastic properties therethrough, thereby resulting in a better overall snug fit of undergarment 26. For example, referring to FIG. 14, the number of bond points per unit area in rear end portion 32 and front end portion 28 can be greater than the number of projections per unit area in intermediate portion 30. This would result in intermediate portion 30 having greater elasticity or stretch properties than end portions 28, 32, so as to provide a snug and comfortable fit in the crotch area. Similarly, only selected zones of rear end portion 32 and/or front end portion 28 can have a greater number of bond points per unit area, thereby selectively controlling the elasticity or stretchability thereof. The immobilization effect can be controlled by either increasing or decreasing the number of bond points per unit area or the surface area of each individual bond point in a unit area.

As the bonded layers exit nip 64, they pass between anvil 78 and cutting roll 80, which has a plurality of blades 82 selectively disposed thereon. Blades 82 are selectively positioned to cut the bonded layers in any configuration, such as a generally trapezoidal configuration.

Although pattern roll 58 with projections 62 is one method of bonding the layers together thermally, other bonding methods are contemplated by the method of the present invention and include ultrasonic bonding, adhesive bonding and other suitable bonding methods. Once the bonded layers pass through nip 64, the elastomeric layer is allowed to relax and to gather the other layers.

In a general embodiment of composite 2 or undergarment 26, there is a thermoplastic liner 4, thermoplastic transfer layer 22, thermoplastic elastomeric layer 6, thermoplastic wicking layer 24, thermoplastic absorbent medium 8, and thermoplastic outer cover 10. With this general embodiment, the temperature at which pattern roll 58 and anvil roll 60 are maintained falls within a range of 0° to about 400° F. The nip pressure at nip 64 is generally between 0 to about 1500 pounds per square inch, and the bond area, as a percentage of the total surface area, is between about 1% to about 50%. The roll speed of pattern roll 58 and anvil 60 can also vary between 0 to about 1,000 feet per minute. As roll speed is increased or decreased, the required temperatures and pressures will also change as a function of the thermoplastic materials making up the various layers.

In a specific form, pattern roll 58 is maintained at a temperature between about 260° F. to about 330° F., and anvil 60 is maintained at a temperature between about 75° F. to about 210° F. The pressure at nip 64 is about 30 to about 80 psi, the roll speed is about 15 to about 30 feet per minute, and the bond area is about 10% to about 20%. These particular parameters apply to a liner 4 made of spunbonded polypropylene having a basis weight of about 0.4 ounces per square yard; wicking layer 24 being a carded web of about 25% by weight polyester and 75% by weight polypropylene with a basis weight of about 50 grams per square meter; elastomeric layer 6 being made of Kraton G-2740X having a basis weight of about 70 grams per square meter; absorbent medium 8 being a mixture of about 75% by weight polyester and 25% by weight of binder and having mixed therewith a superabsorbent having a basis weight of about 16 grams per square meter, the overall absorbent medium 8 having a basis weight of about 70 grams per square meter; and outer cover 10 being a film of polyester having a thickness of about 0.6 mils.

In another form, the temperature of pattern roll 58 is about 150° F. to about 250° F., and the temperature of anvil 60 is about 75° F. to about 210° F. The pressure at nip 64 is about 30 to about 80 psi, the roll speed is about 15 to about 30 feet per minutes, and the bond area is about 10% to about 20%. These parameters apply to a composite 2 or undergarment 26 comprising a liner 4 of spunbonded polyethylene having a basis weight of about 0.4 ounces per square yard; wicking layer 24 being a carded web of about 70% by weight polyester and 30% by weight of a suitable binder, having an overall basis weight of about 50 grams per square meter; elastomeric layer 6 being made of Kraton G-2740X having a basis weight of about 70 grams per square meter; absorbent medium 8 being a web of about 60% by weight fluff pulp and 40% by weight of polyethylene and having mixed therewith a superabsorbent having a basis weight of about 16 grams per square meter, the overall basis weight of absorbent medium 8 being about 70 grams per square meter; and outer cover 10 being a polyethylene film having a thickness of about 0.6 mils.

In another form, pattern roll 58 has a temperature of about 250° F. to about 310° F., and anvil 60 has a temperature of about 60° F. to about 90° F. The pressure at nip 64 is about 20 psi to about 40 psi, the roll speeds about 10 to about 20 feet per minute, and the bond area between about 15% to about 25%. These parameters apply to a composite 2 or undergarment 26 comprising a liner 4 of spunbonded polypropylene having a basis weight of about 0.4 ounces per square yard; a transfer layer 22 being a carded web of about 50% by weight polyester and about 50% by weight polypropylene and having a basis weight of about 30 grams per square meter; elastomeric layer 6 being made of Kraton G-2740X having a basis weight of about 70 grams per square meter; absorbent medium 8 being a web of about 60% by weight wood fluff pulp and about 40% by weight of polyethylene and having a superabsorbent mix therewith having a basis weight of about 16 grams per square meter, the overall basis weight of absorbent medium 8 being about 165 grams per square meter; and outer cover 10 being a polyethylene film having a thickness of about 0.6 mils.

While this invention has been described as having a preferred embodiment, it will be understood that it is capable of further modifications. This application is therefore intended to cover any variations, uses or adaptations of the invention following the general principles thereof, and including such departures from the present disclosure as come within known or customary practice in the art to which this invention pertains and fall within the limits of the appended claims.

What is claimed is:

1. A stretchable absorbent undergarment for absorbing human liquids and waste materials, comprising:
   a liquid-pervious bodyside layer,
   a liquid-impervious outer layer,
   an absorbent layer being disposed between said liquid-pervious bodyside layer and said liquid-impervious outer layer,
   a stretchable layer being disposed between said liquid-pervious bodyside layer and said liquid-impervious outer layer,
   said stretchable layer being stretch bonded to said other layers and forming a plurality of rugosities in said bodyside layer, said outer layer, and said absorbent layer upon relaxation thereof,
   said bonded layers being of a generally trapezoidal shape and having a front end portion that diverges toward a rear end portion, said front end portion being about 25% to about 80% of the width of said rear end portion, said rear end portion being about 20% to about 60% of the length of said bonded layers.

2. The undergarment of claim 1 wherein said rear end portion is about 25% to about 50% of the length of said bonded layers.

3. The undergarment of claim 1 further comprising a liquid transfer layer between said bodyside layer and said absorbent layer for transferring liquid generally in the Z-direction through said bodyside layer and said liquid transfer layer and into said absorbent layer.

4. The undergarment of claim 1 further comprising a liquid wicking layer between said bodyside layer and said absorbent layer for wicking liquid generally in the X- and Y-directions prior to absorption in said absorbent layer.

5. The undergarment of claim 1 wherein said stretchable layer is made pervious with a plurality of apertures.

6. The undergarment of claim 1 wherein said bonded layers are selectively bonded at predetermined areas to control the elasticity thereof.

7. The undergarment of claim 1 wherein the bonded area is from about 1% to about 50% of the total area of said undergarment.

8. The undergarment of claim 1 wherein said layers can have different sizes or shapes.

9. A stretchable absorbent undergarment for absorbing human discharge, comprising:
   a liquid-pervious bodyside layer,
   a liquid-impervious outer layer,
   an absorbent layer disposed between said liquid-pervious bodyside layer and said liquid-impervious outer layer,
   a liquid delivery layer disposed between said liquid-pervious bodyside layer and said liquid-impervious outer layer,
   a stretchable layer disposed between said liquid-pervious bodyside layer and said liquid-impervious outer layer,
   said stretchable layer being stretch bonded to said other layers and forming a plurality of rugosities in said bodyside layer, said outer layer, said absorbent layer, and said liquid delivery layer upon relaxation thereof.

10. The undergarment of claim 9 wherein said bonded layers are of a generally trapezoidal shape.

11. The undergarment of claim 9 wherein said liquid delivery is a transfer layer for transferring liquid generally in the Z-direction.

12. The undergarment of claim 9 wherein said liquid delivery layer is a wicking layer for wicking liquid generally in the X- and Y-directions.

13. The undergarment of claim 9 wherein said stretchable layer is stretched in multiple directions during bonding to said other layers.

14. The undergarment of claim 9 wherein said bonded layers are selectively bonded at predetermined areas to control the elasticity thereof.

15. The undergarment of claim 9 wherein the bonded area is from about 1% to about 50% of the total area of said undergarment.

16. The undergarment of claim 9 wherein said layers are of a different size or shape.

17. A stretchable absorbent undergarment for absorbing human discharge, comprising:
   a liquid pervious bodyside layer,
   a liquid impervious outer layer,
   an abosorbent layer disposed between said liquid pervious bodyside layer and said liquid impervious outer layer, and
   a stretchable layer disposed between said liquid pervious bodyside layer and said liquid impervious outer layer,
   said stretchable layer being stretch bonded in multiple directions to said other layers and forming a plurality of rugosities in said other layers upon relaxation thereof.

18. The undergarment of claim 17 wherein said bonded layers are selectively bonded at predetermined areas to control the elasticity thereof.

19. The undergarment of claim 17 wherein the bonded area is from about 1% to about 50% of the total area of said undergarment.

20. The undergarment of claim 17 further comprising a liquid delivery layer between said bodyside layer and said outer layer.

* * * * *